United States Patent
Shull et al.

(10) Patent No.: US 6,169,076 B1
(45) Date of Patent: Jan. 2, 2001

(54) P-BORONOPHENYLALANINE COMPLEXES WITH FRUCTOSE AND RELATED CARBOHYDRATES AND POLYOLS

(75) Inventors: Brian Shull, Durham; David Spielvogel, Raleigh; Gerald Head, Cary, all of NC (US)

(73) Assignee: Glcosyn Pharmaceuticals, Inc., DE (US)

( * ) Notice: Under 35 U.S.C. 154(b), the term of this patent shall be extended for 0 days.

(21) Appl. No.: 09/282,847

(22) Filed: Mar. 31, 1999

(51) Int. Cl.$^7$ .............................. A61K 31/70; C07H 1/00
(52) U.S. Cl. ............................ 514/23; 514/64; 536/1.11; 536/18.7; 536/124; 568/6
(58) Field of Search ........................... 514/64, 23; 568/6; 536/124, 1.11, 18.7

(56) References Cited

U.S. PATENT DOCUMENTS 5,492,900   2/1996   La Haan ................................ 514/64

OTHER PUBLICATIONS

Allen et al., "Boron dose enhancement for $^{252}$Cf brachytherapy," in *Advances in Neutron Capture Therapy, vol. 1*, Larsson et al. (eds.), pp. 271–274, Elsevier Science B.V. [1997].

Aronoff et al., "Complexation of D–Glucose with Borate," *Carbohydrate Res.* 40: 299–309 [1975].

Barth et al., "Boron Neutron Capture Therapy of Cancer," *Cancer Res.* 50: 1061–1070 [1990].

Barth et al., "Boron Neutron Capture Therapy of Brain Tumors: Past History, Current Status, and Future Potential," *Cancer Invest.* 14: 534–550 [1996].

Chadha et al., "Boron Neutron–Capture Therapy (BNCT) for Glioblastoma Multiforme (GBM) Using the Epithermal Neutron Beam at the Brookhaven National Laboratory," *Int. J. Radiat. Oncol. Biol. Phys.* 40: 829–834 [1998].

Coderre et al., "Selective Targeting of Boronophenylalanine to Melanoma in BALB/c Mice for Neutron Capture Therapy," *Cancer Res.* 47: 6377–6383 [1987].

Coderre et al., "Neutron Capture Therapy of the 9L Rat Gliosarcoma Using the P–Boronophenylalanine–Fructose Complex," *Int. J. Radiation Oncology Biol. Phys.* 30: 643–652 [1994].

Day et al., Cryopreservation and freeze–drying protocols, Methods in Molecular Biology, vol. 38, Humana Press, New Jersey [1995] (Title and Copyright Pages Only).

Duker et al., "($^{13}$C)–Substituted sucrose: $^{13}$C–$^{1}$H and $^{13}$C–$^{13}$C spin coupling constants to assess furanose ring and glycosidic bond conformations in aqueous solution," *Carbohydr. Res.* 249: 281–303 [1993].

Fairchild et al., "Current Status of $^{10}$B–Neutron Capture Therapy: Enhancement of Tumor Dose Via Beam Filtration and Dose Rate, and the Effects of These Parameters on Minimum Boron Content: A Theoretical Evaluation," *Int. J. Radiation Oncology Biol. Phys.* 11: 831–840 [1985].

Flosdorf, Freeze–drying; drying by sublimation, Reinhold Pub. Corp. [1949] (Title and Copyright Pages Only).

Gabel et al., "The Monte–Carlo Simulation of the Biological Effect of the $^{10}$B(n,α)$^{7}$Li Reaction in Cells and Tissue and Its Implications for Boron Neutron Capture Therapy," *Radiation Res.* 111: 14–25 [1987].

Gianotto et al., "Optical Purity Determination of D,L–Boronophenylalanine by High Performance Liquid Chromatography with a Chiral Mobile Phase," in *Progress in Neutron Capture Therapy for Cancer*, Allen et al., (eds.), pp. 247–250, Plenum Press [1992].

Goux, "Complex Isomerization of Ketoses: A 13C NMR Study of the Base–Catalyzed Ring–Opening and Ring–Closing Rates of D–Fructose Isomers in Aqueous Solution," *J. Am. Chem. Soc.* 107: 4320–4327 [1985].

Honda et al., "Increased Selective $^{10}$B–Uptake by Malignant Melanoma Using Systemic Administration of $^{10}$B$_1$–BPA•Fructose Complex," *Progress in Neutron Capture Therapy for Cancer*, Allen et al. (eds.), pp. 421–424, Plenum Press [1992].

Ichihashi et al., "Specific Killing Effect of $^{10}$B$_1$–Para–boronophenylalanine in Thermal Neutron Capture Therapy of Malignant Melanoma: In Vitro Radiobiological Evaluation," *J. Invest. Dermatol.* 78: 215–218 [1982].

James et al., "Saccharide Sensing with Molecular Receptors Based on Boronic Acid," *Angew. Chem. Int. Ed. Engl.* 35: 1910–1922 [1996].

James et al., "Novel Photoinduced Electron–transfer Sensor for Saccharides based on the Interaction of Boronic Acid and Amine," *J. Chem. Soc., Chem. Commun.*, pp. 477–478 [1994].

Javid et al., "The Possible Use of Neutron–Capturing Isotopes Such as Boron 10 in the Treatment of Neoplasms. II. Computation of the Radiation Energies and Estimates of Effects in Normal and Neoplastic Brain," *J. Clin. Invest.* 31: 604–610 [1952].

Kinoshita et al., "Complex formation of Phenylboronic Acid Derivatives with Aldopentoses and Oligosaccharides," in *Progress in Neutron Capture Therapy for Cancer*, Allen et al. (ed.), pp. 243–246, Plenum Press, New York [1992].

(List continued on next page.)

Primary Examiner—Elli Peselev
(74) Attorney, Agent, or Firm—Medlen & Carroll, LLP

(57) ABSTRACT

The present invention is directed to salt-free and essentially salt-free p-boronophenylalanine-carbohydrate or p-boronophenylalanine-polyol complexes, as well as methods for making such compounds. In addition, the present invention provides methods for substantially solubilizing freeze-dried p-boronophenylalanine-carbohydrate and p-boronophenylalanine-polyol complexes. The present invention further provides compositions and methods for enhancing the solubility of boronophenylalanine.

21 Claims, 3 Drawing Sheets

OTHER PUBLICATIONS

Kirihata et al., "An Efficient Synthesis of p–Boronophenylalanine and its Homologues by the Reaction of Ethyl Isocyanoacetate with a p–Formylbenzeneborononic acid Derivative," in *Cancer Neutron Capture Therapy*, Mishima (ed.), pp. 99–104, Plenem Press [1996].

Kobayashi et al., "Analytical Calculation of Boron–10 Dosage in Cell Nucleus for Neutron Capture Therapy," *Radiation Res.* 91: 77–94 [1982].

Kondo et al., "Specific Complexation of Dissacharides with Diphenyl–3,3'–diboronic Acid that Can Be Detected by Circular Dichroism," *Tetrahedron* 48: 8239–8252 [1992].

Krvidin and Kalabin, "Structural Applications of One–Bond Carbon–Carbon Spin–Spin Coupling Constants," in *Progr. NMR Spectroscopy*, Emsley et al. (eds.), vol. 21, pp. 293–448 [1989].

Kuivila et al., "Areneborates From Diols and Polyols," *J. Org. Chem.* 19: 780–783 [1954].

LaHaan et al., "Cardiovascular Toxicities Associated with Intravenous Administration of P–Boronophenylalanine Formulations," in *Advances in Neutron Therapy*, Soloway et al. (eds.), pp. 513–517, Plenum Press, New York [1993].

Locher, "Biological Effects and Therapeutic Possibilities of Neutrons," *Am. J. Roenten. Rad. Ther.* 36: 1–13 [1936].

Lorand et al., "Polyol Complexes and Structure of the Benzeneborate Ion," *J. Org. Chem.* 24: 769–774 [1959].

Lorvidhaya et al., "Boron neutron capture therapy in advanced cancer of the cervix," in *Advances in Neutron Capture Therapy, vol. II*, Larsson et al. (eds.), pp. 540–544, Elsevier Science B. V. [1997].

Maruyama et al., "Clinical Trial of $^{252}$Cf Neutron Brachytherapy vs. Conventional Radiotherapy for Advanced Cervical Cancer," *Int. J. Radiat. Oncol. Biol. Phys.* 11: 1475–1482 [1985].

Matalka et al., "Boron Neutron Capture Therapy of Intracerebral Melanoma Using Boronophenylalanine as a Capture Agent," *Cancer Res.* 53: 3308–3313 [1993].

Mehta and Lu, "Targeted Drug Delivery for Boron Neutron Capture Therapy," *Pharm. Res.* 13:344–351 [1996].

Mellor, *Fundamentals of Freeze–drying*, Academic Press, New York [1978] (Title and Copyright Pages Only).

Miller and Horton, "Advantage of using Cf–252 combined with Gd–157 for treatment of bulky tumors," in *Advances in Neutron Capture Therapy, vol. II*, Larsson et al. (eds.), pp. 545–546, Elsevier Science B. V. [1997].

Mishima et al., Advances in the Control of Human Cutaneous Primary and Metastatic Melanoma by Thermal Neutron Capture Therapy, in *Progess in Neutron Capture Therapy for Cancer*, Allen et al. (eds.), pp. 577–583, Plenum Press [1992].

Mori et al., "Complex Formation of p–Boronophenylalanine With Some Monosaccharides," *Pig. Cell Res.* 2: 273–277 [1989].

Norrild and Eggert, "Boronic acids as fructose sensors. Structure determination of the complexes involved using $^1J_{cc}$ coupling constants," *J. Chem. Soc. Perkin Trans* 2, pp. 2583–2588 [1996].

Norrild and Eggert, "Evidence for Mono– and Bisdentate Boronate Complexes of Glucose in the Furanose Form. Application of $^1J_{cc}$ coupling constants as a Structural Probe," *J. Am. Chem. Soc.* 117: 1479–1484 [1995].

Packer et al., "Boron Neutron Capture Therapy of Anterior Chamber Melanoma with p–Boronophenylalanine," *Invest Ophthalmol. Vis. Sci.* 33: 395–403 [1992].

Pelmore et al., "N.m.r. studies of complexes formed by D–fructose and borate ions in aqueous solution," *Carbohydr. Res.* 155: 206–211 [1986].

Samsel et al., "Enantioselective Synthesis of L–(–)–4–Boronophenylalanine (L–BPA) By Asymmetric Catalyic Hydrogenation," in *Progress in Neutron Capture Therapy for Cancer*, Allen et al. (eds.), pp. 251–254, Plenum Press [1992].

Saris et al., "Boron Neutron Capture Therapy for Murine Malignant Gliomas," *Cancer Res.* 52: 4672–4677 [1992].

Schnieder et al., "Distribution of Furanoid and Pyranoid Tautomers of D–Fructose in Water, Dimethyl Sulfoxide, and Pyridine via $^1$H NMR Intensities of Anomeric Hydroxy Groups in [D$^6$] DMSO," *Liebigs Ann. Chem.*, pp. 2443–2453 [1985].

Shi et al., "Gadolinium as a neutron capture therapy agent," *Med. Phys.* 19: 733–744 [1992].

Shinkai et al., "Molecular Recognition of Mono– and Di–saccharides by Phenylboronic Acids in Solvent Extraction and as a Monolayer," *J. Chem. Soc., Chem. Commun.*, pp. 1039–1041 [1991].

Shpikalov et al., *Nucl. Sci. Appl.* 4: 419 [1991] (Reference could not be obtained at this time. Will provide reference at a later time should the Examiner desire a copy).

Snyder et al., "Synthesis of Aromatic Boronic Acids. Aldehydo Boronic Acids and a Boronic Acid Analog of Tyrosine," *J. Am. Chem. Soc.* 80: 835–338 [1958].

Snyder and Serianni, "Synthesis and N.M.R.–Spectral Analysis of Unenriched and [1–$^{13}$C]–Enriched 5–Deoxypentoses and 5–O–Methylpentoses," *Carbohydr. Res.* 163: 169–188 [1987].

Sweet et al., "The Uses of Nuclear Disintegration in the Diagnosis and Treatment of Brain Tumor," *N. Engl. J. Med.* 245: 875–878 [1951].

Tsukagoshi et al., "Specific Complexation with Mono– and Disaccharides That Can Be Detected by Circular Dichroism," *J. Org. Chem.* 56: 4089–4091 [1991].

van den Berg et al., "The structure and (local) stability constants of borate esters of mono– and di–saccharides as studied by $^{11}$B and $^{13}$C NMR spectroscopy," *Carbohydr. Res.* 253: 1–12 [1994].

van Duin et al., "Studies on Borate Esters I: The pH Dependence of the Stability of Esters of Boric Acid and Borate in Aqueous Medium as Studied by $^{11}$B NMR," *Tetrahedron* 40: 2901–2911 [1984].

van Duin et al., "Studies on Borate Esters II: Structure and Stability of Borate Esters of Polyhydroxycarboxylates and Related Polyols in Aqueous Alkaline Media as Studied by $^{11}$B NMR," *Tetrahedron* 41: 3411–3421 [1985].

Verchere et al., "Stability Constants of Borate Complexes of Oligosaccharides," *Polyhedron* 6: 1415–1420 [1987].

Wade, Jr., Organic Chemistry, pp. 383–384, Prentice–Hall, Inc. [1987].

Wood et al., "Synthesis, and P.M.R. and Mass Spectra of Some Boronic Esters of Carbohydrates," *Carbohydrate Res.* 36: 247–256 [1974].

Yoshino et al., Proc. 2nd International Symp. on Neutron Capture Therapy, p. 291 [1986] (Reference could not be obtained at this time. Will provide this reference at a later date should the Examiner desire a copy).

Yoshino et al., "Improvement of solubility of p–boronophenylalanine by complex formation with monosaccharides," *Strantenthen Onkol.* 165: 127–129 [1989].

Duker and Serianni, "($^{13}$C)–Substituted sucrose: $^{13}$C–$^1$H and $^{13}$C–$^{13}$C spin coupling constants to assess furanose ring and glycosidic bond conformations in aqueous solution," *Carbohydrate Res.* 249: 281–303 (1993).

Mohler and Czarnik, "α–Amino Acid Chelative Complexation by an Arylboronic acid," *J. Am. Chem. Soc.* 115: 7037–7038 (1993).

3 (5%)

2 (13%)

1 (82%)

β-D-fructopyranose        β-D-fructofuranose (3.2)

Maltulose (3.1)           Lactulose (3.0)

Sorbose (2.7)             Palatinose (2.6)

Turanose (1.6)            Sucrose (ND)

Leucrose (1.7)

P-BORONOPHENYLALANINE COMPLEXES WITH FRUCTOSE AND RELATED CARBOHYDRATES AND POLYOLS

FIELD OF THE INVENTION

The present invention relates to the preparation of salt-free or essentially salt-free p-boronophenylalanine complexes with enhanced solubility.

BACKGROUND OF THE INVENTION

Neutron capture therapy (NCT), first postulated by Locher in 1936 (Locher, *Am. J. Roenten. Rad. Ther.* 36: 1–13 [1936]) and Sweet (Javid et al., *J. Clin. Invest.* 31: 603 [1952]); Sweet et al., *N. Engl. J. Med.* 245: 875 [1951]), is a binary system for treating tumors in which a chemical agent and thermal or isothermal neutrons are directed to a tumor where they combine to release a lethal dose of radiation to the cell. A commonly used chemical agent usually includes at least one $^{10}$B atom, although other compounds (i.e., $^{157}$Gd) have also been investigated (Shi et al., *Med. Phys.* 19: 733 [1992]; Miller and Horton, in *Advances in Neutron Capture Therapy, Vol II*, Larsson et al., eds., Elsevier Science B. V., pp. 545–546 [1997]). The neutron source is typically generated by a nuclear reactor, accelerator or generator, although other sources (i.e., $^{252}$Cf) have been explored (See e.g., Maruyama et al., *Int. J. Radiat. Oncol. Biol. Phys.* 11: 1475 [1985]; Shpikalov et al., *Nucl. Sci. Appl.* 4: 419 [1991]; Lorvidhaya et al., in *Advances in Neutron Capture Therapy, vol II*, page 540, Larsson et al., eds., Elsevier Science B. V. [1997]; Miller et al., in *Advances in Neutron Capture Therapy, vol. II*, pp. 545–546, Larsson et al., eds., Elsevier Science B. V. [1997]; Barth et al., *Cancer Res.* 50: 1061–1070 [1990]; Allen et al., in *Advances in Neutron Capture Therapy, vol. I*, pp. 271–274, Larsson et al., eds., Elsevier Science B. V. [1997]).

Boron neutron capture therapy (BNCT) is a form of radiochemotherapy that is becoming increasingly important for the treatment of malignant gliomas, malignant melanomas and other forms of cancer. BNCT involves administration of a boron compound ($^{10}$B) followed by neutron irradiation of the tumor cells or organ. The boron captures a neutron ($n_{th}$), which results in the release of ionizing helium and lithium ions that are highly damaging and usually lethal to the host cell (Kobayashi et al., *Radiation Res.* 91: 77–94 [1982]; Garth et al., *Radiation Res.* 111: 14–25 [1987]). For BNCT to be successful, a large number of $^{10}$B atoms must be localized on or preferably within the target cells, and a sufficient number of thermal neutrons must reach and be absorbed by the $^{10}$B atoms to sustain a lethal reaction.

Targeted delivery of boron to tumors is a critical prerequisite for successful BNCT. Thus, the development of tumor-localizing boron compounds continues to be of interest to researchers in this field. (See e.g., Saris et al., *Cancer Res.* 52: 4672–4677 [1992]; Mehta and Lu, *Pharm Res.* 13:344–351 [1996]; Barth et al., *Cancer Invest.* 14: 534–550 [1996]; Chadha et al., *Int. J Radiat. Oncol. Biol. Phys.* 40: 829–834 [1998]; Fairchild et al., *Int. J Radiation Oncology Biol. Phys.* 11: 831–840 [1985]).

p-Boronophenylalanine (p-BPA) was initially proposed as a boron delivery drug for BNCT of malignant melanoma because it was postulated that this amino acid would selectively accumulate in melanoma cells by mimicking phenylalanine, an amino acid precursor of melanin. p-Boronophenylalanine has been shown to be selectively taken up by melanoma cells (See e.g., Packer et al., *Invest Ophthalmol. Vis. Sci.* 33: 395–403 [1992]; Coderre et al., *Cancer Res.* 47: 6377–6383 [1987]). Intravenous infusion of p-BPA was a possible route for delivering p-BPA to tumor cells, but was not widely used because p-BPA exhibits poor water solubility at physiological pH (7.4). (See e.g., U.S. Pat. No. 5,492,900 to LaHaan; LaHaan et al., in *Advances in Neutron Therapy*, pp. 513–517, Soloway et al., eds., Plenum Press, New York [1993]). p-Boronophenylalanine has a solubility of 1.6 g/L in water, which is insufficient for medical uses (Mori et al., *Pig. Cell Res.* 2: 273–277 [1989]).

Hydrochloric acid salts of p-BPA have been used to increase p-BPA solubility (See e.g., Ichihashi et al., *J. Invest. Dermatol.* 78: 215 [1982]; Yoshino et al., *Proc. 2nd International Symp. on Neutron Capture Therapy*, p. 291 [1986]). However, the acidity imparted by hydrochloric acid salts of p-BPA (e.g., a 0.1 M solution is reported to have a pH value of approximately 1.5), causes pain to patients injected with p-BPA solution of this acidity (Mori et al., supra; Yoshino et al., *Strantenthen Onkol.* 165: 127–129 [1989]). Therefore, it is desirable to find methods of increasing the solubility of p-BPA at physiological pH.

One method for increasing p-BPA solubility is the use of organic complexes. Complex formation of boric acid, borate and aromatic boronic acids with different polyols has been known for some time (See e.g., Kuivila et al., *J. Org. Chem.* 19: 780 [1954]; Lorand et al., *J. Org. Chem.* 24: 769 [1959]; Aronoff et al., *Carbohydrate Res.* 40: 299–309 [1975]; van Duin et al., *Tetrahedron* 40: 2901–2911 [1984]; van Duin et al., *Tetrahedron* 41: 3411–3421 [1985]; Shinkai et al., *J. Chem. Soc., Chem. Commun.*, pp. 1039–1041 [1991]; Verchere et al., *Polyhedron* 6: 1415–1420 [1987]; Kondo et al., *Tetrahedron* 48: 8239–8252 [1992]; Shiomi et al., *J. Chem. Soc. Perkin Trans.*, pp. 2111–2117 [1993]; Tsukagoshi et al., *J. Org. Chem.* 56: 4089–4091 [1991]; James et al., *Angew. Chem. Int. Ed. Engl.* 35: 1910–1922 [1996]; Wood et al., *Carbohydrate Res.* 36: 247–256 [1974]; James et al., *J. Chem. Soc., Chem. Commun.*, pp. 477–478 [1994]; Kinoshita et al., in *Progress in Neutron Capture Therapy for Cancer*, pp. 243–246, Allen et al., eds., Plenum Press, New York [1992]). The solubility effects of monosaccharides and polyols allow for more efficient intravenous use of p-BPA (See e.g., Mori et al., supra; U.S. Pat. No. 5,492,900, supra; Honda et al., in *Progress in Neutron Capture Therapy for Cancer*, Allen et al., eds., Plenum Press, page 421 [1992]; Mishima et al., in *Progress in Neutron Capture Therapy for Cancer*, Allen et al. (eds.), Plenum Press, page 577 [1992]; Matalka et al., *Cancer Res.* 53: 3308 [1993]). For example, studies have shown that systemic administration of p-BPA-fructose complex increases the $^{10}$B uptake in a murine melanoma model (Coderre et al., *Int. J. Radiation Oncology Biol. Phys.* 30: 643–652 [1994]).

Furthermore, p-BPA exists in different forms at different pH values, and complexing of p-BPA with monosaccharides is a pH dependent process. Recent studies have reported a method of solubilizing p-BPA at neutral pH using fructose, to yield a p-BPA-fructose complex (See, Mori et al., supra; U.S. Pat. No. 5,492,900, supra). These methods involve mixing equimolar amounts of p-BPA and fructose in water, increasing the pH to about 10 to dissolve all solids, and subsequent pH adjustment to 7.4 using a concentrated acid (i.e., hydrochloric acid). However, the current methods produce roughly one equivalent of NaCl (depending on how high the pH is raised), thus greatly exceeding its iso-osmotic point with blood and may be partially responsible for the toxicity observed when administered intravenously (LaHann et al., in *Advances in Neutron Capture Therapy*, Soloway et al., eds. Plenum Press, page 513 [1993]). Additionally, the solution must be used within two days of its preparation and requires a trained technician working with concentrated solutions of HCl and NaOH in an aseptic laboratory environment in close proximity to the treatment area.

Thus, it is desirable to find methods of making p-BPA complexes that are free of NaCl salts. Additionally, by understanding the chemical nature of the complex of p-BPA with fructose, other new complexes may be discovered. It is also desirable to find new p-BPA complexes that can be stored for a long time, and that eliminate the need for working with concentrated acids and bases.

SUMMARY OF THE INVENTION

The present invention relates to salt-free and essentially salt-free p-boronophenylalanine-carbohydrate complexes and p-boronophenylalanine-polyol complexes, and methods of making such compounds, both as solutions and solids. The present invention also relates to methods of substantially solubilizing freeze-dried p-boronophenylalanine-carbohydrate and p-boronophenylalanine-polyol complexes.

In preferred embodiments, the present invention relates to l-p-boronophenylalanine-carbohydrate or polyol complexes. In other preferred embodiments, the present invention relates to racemic (d,l)-p-boronophenylalanine-carbohydrate or polyol complexes.

The present invention relates to methods of making an essentially salt-free or salt-free (p-boronophenylalanine)-carbohydrate complex, comprising the steps of: a) providing: i) p-boronophenylalanine, ii) water, iii) a carbohydrate, iv) a base, and v) an ion-exchange media; b) mixing p-boronophenylalanine, water, carbohydrate and base to produce a basic solution such that p-boronophenylalanine and the carbohydrate are solubilized therein; c) adding ion-exchange media to the basic solution comprising p-boronophenylalanine and the carbohydrate, thereby adjusting the pH to the range of between about 7.3 and 7.5, to produce a mixture at physiological pH; and d) removing the ion-exchange media from the mixture to produce a salt-free or essentially salt-free (p-boronophenylalanine)-carbohydrate complex in solution.

In some embodiments, the method of the present invention further comprises the step of: f) freeze-drying the salt-free or essentially salt-free (p-boronophenylalanine)-carbohydrate complex in solution, to produce a freeze-dried salt-free or essentially salt-free (p-boronophenylalanine)-carbohydrate complex.

In one embodiment, the ion-exchange media is removed by filtration. In another embodiment, the ion-exchange media is removed by decanting.

In preferred embodiments, p-boronophenylalanine is selected from the group consisting of racemic (d,l)-p-boronophenylalanine and l-p-boronophenylalanine.

In one embodiment, ion-exchange media is removed by filtration. In other embodiments, ion-exchange media is removed by decanting. In preferred embodiments, the ion-exchange media is an ion-exchange resin. In particular embodiments, the ion-exchange resin is Dowex 50WX4-50 ion-exchange resin.

In some embodiments, the molar ratio of p-boronophenylalanine to carbohydrate is approximately 1:1.1. In alternative embodiments, the molar ratio of p-boronophenylalanine to carbohydrate is 1 equivalent and an excess of up to 8 equivalents of carbohydrate.

In preferred embodiments, p-boronophenylalanine, water, carbohydrate and base are mixed to produce a basic solution having a pH of between about 8 and 10. Bases with physiologically acceptable counter-ions are used in preferred embodiments, which include, but are not limited to NaOH, KOH, Ca(OH)$_2$, and Mg(OH)$_2$.

Carbohydrates complexed to p-boronophenylalanine include, but are not limited to monosaccharides and disaccharides. In some embodiments, the monosaccharides is selected from the group consisting of fructose, sorbose, ribose, galactose, glucose, mannose, 2-deoxygalactose and 2-deoxyglucose. In alternative embodiments, the disaccharides is selected from the group consisting of maltulose, lactulose, palatinose, leucrose, turanose, lactose and maltose.

The present invention relates to methods of making an essentially salt-free or salt-free (p-boronophenylalanine)-polyol complex, comprising the steps of: a) providing: i) p-boronophenylalanine, ii) water, iii) a polyol, iv) a base, and v) an ion-exchange media; b) mixing p-boronophenylalanine, water, polyol and base to produce a basic solution such that p-boronophenylalanine and the polyol are solubilized therein; c) adding ion-exchange media to the basic solution comprising p-boronophenylalanine and the polyol, thereby adjusting the pH to the range of between about 7.3 and 7.5, to produce a mixture at physiological pH; and d) removing the ion-exchange media from the mixture to produce an essentially salt-free or salt-free (p-boronophenylalanine)-polyol complex in solution.

In some embodiments, the method of the present invention further comprises the step of: f) freeze-drying the essentially salt-free or salt-free (p-boronophenylalanine)-polyol complex in solution, to produce a freeze-dried essentially salt-free or salt-free (p-boronophenylalanine)-polyol complex.

In one embodiment, the ion-exchange media is removed by filtration. In another embodiment, the ion-exchange media is removed by decanting.

In preferred embodiments, p-boronophenylalanine is selected from the group consisting of racemic (d,l)-p-boronophenylalanine and l-p-boronophenylalanine.

In one embodiment, ion-exchange media is removed by filtration. In other embodiments, ion-exchange media is removed by decanting. In preferred embodiments, the ion-exchange media is an ion-exchange resin. In particular embodiments, the ion-exchange resin is Dowex 50WX4-50 ion-exchange resin.

In some embodiments, the molar ratio of p-boronophenylalanine to polyol is approximately 1:1.1. In alternative embodiments, the molar ratio of p-boronophenylalanine to polyol is 1 equivalent and an excess of up to 8 equivalents of polyol.

In preferred embodiments, p-boronophenylalanine, water, polyol and base are mixed to produce a basic solution having a pH of between about 8 and 10. Bases with physiologically acceptable counter-ions are used in preferred embodiments, which include, but are not limited to NaOH, KOH, Ca(OH)$_2$, and Mg(OH)$_2$.

Polyols complexed to p-boronophenylalanine include, but are not limited to, sorbitol, mannitol, dulcitol, xylitol, adonitol and threitol.

The present invention relates to compositions comprising an essentially salt-free or salt-free (p-boronophenylalanine)-carbohydrate complex. Carbohydrates complexed to p-boronophenylalanine include, but are not limited to monosaccharides, disaccharides, fructose, sorbose, ribose, galactose, glucose, mannose, 2-deoxygalactose, 2-deoxyglucose, maltulose, lactulose, palatinose, leucrose, turanose, lactose and maltose. In preferred embodiments, the salt-free (p-boronophenylalanine)-carbohydrate complex is in solution.

In other preferred embodiments, the essentially salt-free or salt-free (p-boronophenylalanine)-carbohydrate complex is freeze-dried. Freeze-dried salt-free p-boronophenylalanine-carbohydrate complexes include, but are not limited to l-p-boronophenylalanine-d-fructose complex, l-p-boronophenylalanine-d-sorbose complex, l-p-boronophenylalanine-d-maltulose complex, l-p-boronophenylalanine-d-lactulose complex, and l-p-boronophenylalanine-d-palatinose complex.

The present invention also relates to compositions comprising an essentially salt-free or salt-free (p-boronophenylalanine)-polyol complex. Polyols complexed to p-boronophenylalanine, include but are not limited to sorbitol, mannitol, dulcitol, xylitol, adonitol and threitol. In preferred embodiments, the essentially salt-free or salt-free (p-boronophenylalanine)-polyol complex is in solution. In other preferred embodiments, the essentially salt-free or salt-free (p-boronophenylalanine)-polyol complex is freeze-dried. Freeze-dried essentially salt-free or salt-free p-boronophenylalanine-polyol complexes include, but are not limited to l-p-boronophenylalanine-d-sorbitol complex, l-p-boronophenylalanine-d-mannitol complex, l-p-boronophenylalanine-dulcitol complex, and l-p-boronophenylalanine-xylitol complex.

Furthermore, the present invention relates to methods of substantially solubilizing freeze-dried essentially salt-free or salt-free (l-p-boronophenylalanine)-carbohydrate or polyol complexes, comprising the steps of: a) providing, in any order: i) a freeze-dried salt-free (l-p-boronophenylalanine)-carbohydrate or polyol complex, and ii) a solvent selected from the group consisting of water, isotonic saline, and dilute saline; and b) substantially solubilizing the freeze-dried salt-free (l-p-boronophenylalanine)-carbohydrate or polyol complex with solvent, to provide an iso-osmotic solution.

DESCRIPTION OF THE INVENTION

Figure 1:
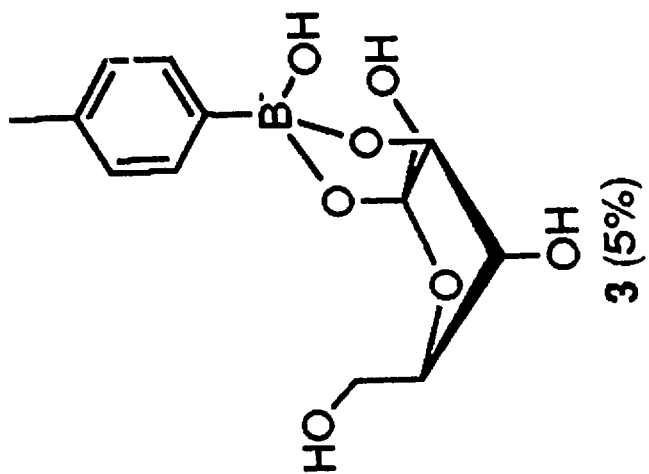
FIG. 1 shows proposed structures of p-tolylboronic acid and fructose complexes in aqueous alkaline solution (pD= 11–12).
Figure 1:
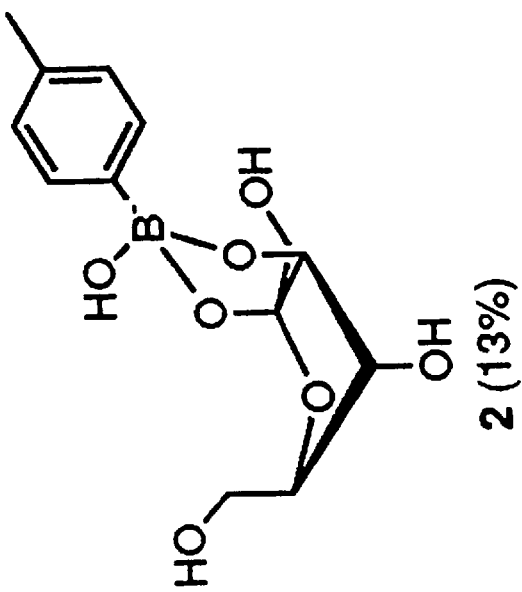
Figure 1:
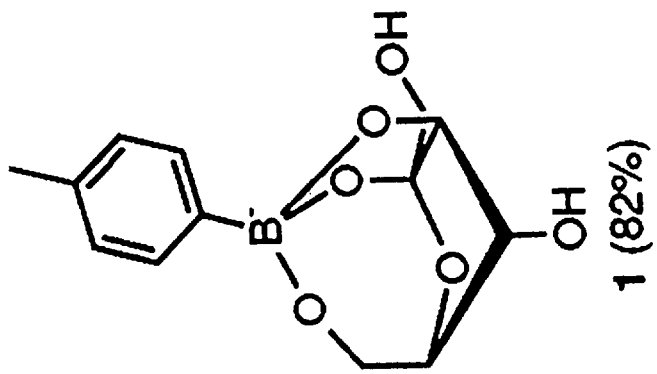

The present invention relates to composition and methods of enhancing the solubility of boronophenylalanine. In particular, the present invention relates to composition and methods of making p-boronophenylalanine (p-BPA)-carbohydrate or polyol complexes as essentially salt-free or salt-free isolated solids, or as essentially salt-free or salt-free complexes in solution. In preferred embodiments, the present invention relates to l-p-boronophenylalanine-carbohydrate or polyol complexes. In other preferred embodiments, the present invention relates to racemic (d,l)-p-boronophenylalanine-carbohydrate or polyol complexes.

In preferred embodiments, the p-boronophenylalanine (p-BPA)-carbohydrate or polyol complexes are substantially dissolved in a solvent, and less than 1% of the solid is suspended.

It is contemplated that the presently claimed invention would reduce both costs and risks for the clinics using the p-BPA monosaccharide complex. The present invention removes the risk involved in handling strong acids and bases when preparing p-BPA solution with a monosaccharide, or with related carbohydrates and polyols, and also removes any concerns about whether the solution has been properly neutralized or not. In addition, the present invention is salt-free or essentially salt-free, and can be administered as an intravenous solution with either isotonic saline, with a buffered salt solution, or with water.

The description of the invention is divided into I) Methods; and II) Mechanistic and Structural Determinations of the Complexes of the Present Invention. Each section will be discussed in turn below.

I. Methods $^{10}B$ enriched p-boronophenylalanine (p-BPA), with an optical purity >99% can be prepared using known procedures (See e.g., Snyder et al., *J. Am. Chem. Soc.* 80: 835 [1958]; Samsel et al., in *Progress in Neutron Capture Therapy for Cancer*, Allen et al, eds., Plenum Press, page 251 [1992]; Kirihata et al., in *Cancer Neutron Capture Therapy*, Mishima, ed., Plenum Press, page 99 [1996]; Gianotto et al., in *Progress in Neutron Capture Therapy for Cancer*, Allen et al., eds., Plenum Press, pp. 247–250 [1992]), or purchased commercially (e.g., RYSCOR [Raleigh, N.C.]; Boron Biologicals, Inc. [Raleigh, N.C.]; Ash Stevens [Detroit, Mich.]; Katchem, ltd. [Czech Republic]).

p-Boronophenylalanine, water, carbohydrate or polyol and base are mixed together to produce a basic solution such that p-boronophenylalanine and the carbohydrate or polyol are substantially solubilized therein (e.g., pH of between 8 and 10). It is not intended that p-boronophenylalanine, water, base, and the carbohydrate or polyol be mixed in a particular order. The ion-exchange media is then added to the basic solution, thereby adjusting the pH to physiological pH (e.g., pH of between 7.3 and 7.5). After adjusting the pH of the solution to physiological pH, the ion-exchange media is removed by filtration or decanting, to produce a salt-free or essentially salt-free solution of the p-BPA-carbohydrate or the p-BPA-polyol complex. Freeze-drying of the solution gives an essentially salt-free or salt-free p-BPA complex as a white solid. (Methods for freeze-drying are well known in the art. See e.g., Flosdorf, Freeze-drying; drying by sublimation, Reinhold Pub. Corp., 1949; Mellor, Fundamentals of Freeze-drying, Academic Press, New York, 1978; and Day et al., Cryopreservation and freeze-drying protocols, Methods in Molecular Biology, vol. 38, Humana Press, New Jersey, 1995).

It is important that the ion-exchange media is added as the last reagent to the mixture of p-boronophenylalanine, base, and the carbohydrate or polyol, for successful solubilization. It is also important that the ion-exchange media is added carefully to the basic solution comprising p-BPA and the carbohydrate or polyol. The approach of simply running the p-BPA carbohydrate or polyol complex through an ion-exchange column fails due to a lack of control in the pH, resulting in the removal of all sodium cations, lowering of the pH of the solution to roughly 6.5, and the precipitation of p-BPA. To prevent the precipitation of p-BPA, small amounts of ion-exchange media are added to the solution, with careful monitoring of the pH of the solution.

In preferred embodiments, the present invention p-boronophenylalanine is selected from the group consisting of racemic (d,l)-p-boronophenylalanine and l-p-boronophenylalanine.

In preferred embodiments, the ion-exchange media is an ion-exchange resin. In particular embodiments, the ion-exchange resin is a Dowex50WX4-50 ion-exchange resin.

It is not intended that the bases used be limited to particular bases. In preferred embodiments, the base comprises physiologically acceptable counter-ions, and is selected from the group consisting of NaOH, KOH, $Ca(OH)_2$ and $Mg(OH)_2$.

In one embodiment, p-BPA is first suspended in water, followed by addition of varying amounts of carbohydrate or polyol in conditions such that the solids substantially dissolve, and the pH of the resulting solution is adjusted to physiological pH using an ion-exchange media. For carbohydrates and polyols that bind strongly with p-BPA, a slight excess (i.e., approximately 1.1 eq) to p-BPA is sufficient. The slight excess is used to compensate for the slight impurities found in commercially available carbohydrates and polyols (e.g., carbohydrate or polyol is usually supplied in 98% purity). The slight excess also compensates for less than a 100% binding between p-BPA and the carbohydrate or polyol. For carbohydrates and polyols that do not bind as strongly with p-BPA, up to 8 equivalents or more is necessary.

In other embodiments, p-BPA and the carbohydrate or polyol are suspended together in water. One equivalent of base (i.e., 0.5 M NaOH) is added dropwise to the suspension of p-BPA and carbohydrate or polyol, and the slurry is gently warmed until all the solids substantially dissolve. Additional amounts of base may be added dropwise if p-BPA does not dissolve completely. The pH of the solution is monitored and increased to a pH between 8 and 10, to produce a p-BPA-carbohydrate or p-BPA-polyol complex in basic solution. The pH of the basic solution is then adjusted to physiological pH in the range of between 7.3 and 7.5, by the addition of an ion-exchange media to the p-BPA-carbohydrate or p-BPA-polyol complex, to provide an essentially salt-free or salt-free p-BPA-carbohydrate or polyol complexes.

It is also contemplated that p-boronophenylalanine be added to an ice cold, basic solution of the carbohydrate or polyol, and the resultant solution, with a pH of between about 8 to 10, can be neutralized with an ion-exchange media, thereby adjusting the resulting pH to physiological pH, to provide an essentially salt-free or salt-free p-BPA carbohydrate or polyol complexes.

It is contemplated that the carbohydrates used for complexing p-BPA include monosaccharides and disaccharides. Monosaccharides can take on either a pyranose or furanose ring form and include, but are not limited to fructose, sorbose, ribose, galactose, glucose, mannose, 2-deoxygalactose, and 2-deoxyglucose. Disaccharides include, but are not limited to, maltulose, lactulose, palatinose, leucrose, turanose, lactose, and maltose. Polyols of the present invention include, but are not limited to, mannitol, sorbitol, dulcitol, and xylitol.

When complex formation is strong, as seen for fructose and sorbose, or when a large excess of another carbohydrate or polyol is used, all of the p-BPA remains in solution at a pH of 7.4, and approximately 90% of the p-BPA is present as its sodium carboxylate, with the remainder as its free acid. The ratio of free p-BPA to p-BPA:carbohydrate complex can be determined by integration of the aromatic protons resonances (p-BPA, 7.73 and 7.33 ppm; p-BPA-carbohydrate complex, 7.5 and 7.2 ppm) in the $^1H$ NMR spectrum using $D_2O$ buffered to physiological pH as the solvent. A minimum of five measurements for each carbohydrate at various concentrations and p-BPA:carbohydrate ratios were taken, and the equilibrium constant calculated (Table 1 and Table 2). Likewise, complex formation constants for p-BPA and some polyols have been calculated (Table 3).

TABLE 1

Complex Formation Constants for p-BPA and Some Monosaccharides.

| Monosaccharide | log $K_{eq}$[a] |
|---|---|
| Fructose | 3.2 |
| Sorbose | 2.7 |
| Ribose | 1.8 |
| Galactose | 1.6 |
| Glucose | 1.4 |
| Mannose | 1.3 |
| 2-Deoxygalactose | 0.6 |
| 2-Deoxyglucose | <0 |

[a]All values were determined for L-p-BPA by integration of aryl protons in the $^1H$ NMR spectrum ($D_2O$, pH buffered at 7.4).

TABLE 2

Complex Formation Constants for p-BPA and Some Disaccharides

| Disaccharide | log $K_{eq}$[a] |
|---|---|
| Maltulose | 3.1 |
| Lactulose | 3.0 |
| Palatinose | 2.6 |
| Leucrose | 1.7 |
| Turanose | 1.6 |
| Lactose | 0.2 |
| Maltose | 0.2 |

[a]All values were determined for L-p-BPA by intergration of aryl protons in the $^1H$ NMR spectrum ($D_2O$, pH buffered at 7.4).

TABLE 3

Complex Formation Constants for p-BPA and Some Polyols

| Polyol | log $K_{eq}$[a] |
|---|---|
| Sorbitol | 3.2 |
| Mannitol | 2.7 |
| Xylitol | 2.5 |
| Adonitol | 1.7 |
| D,L Threitol | 1.3[b] |

[a]All values were determined for L-p-BPA by integration of aryl protons in the $^1H$ NMR spectrum ($D_2O$, pH buffered at 7.4).
[b]Estimated value.

II. Mechanistic Studies and Structural Determinations of the Complexes of the Present Invention Analysis of the $^{13}C$ NMR spectra of the l-p-BPA-fructose complex in conjunction with a study on the complexation ability of disaccharides (Table 2), particularly those containing a fructose moiety, provides some information to the structure of the l-p-BPA complex, although it is not necessary to understand the mechanism in order to use the present invention, and it is not intended that the present invention be so limited. In water, fructose exists as a complex mixture of five isomers, in which β-d-fructopyranose predominates over β-d-fructofuranose and α-d-fructofuranose (See e.g., van den Berg et al., *Carbohydr. Res.* 253: 1 [1994]; Pelmore et al., *Carbohydr. Res.* 155: 206 [1986]; Schnieder et al., *Liebigs Ann. Chem.*, p. 2443 [1985]; Goux, W. J., *J. Am. Chem. Soc.* 107: 4320 [1985]). Small amounts of α-d-fructopyranose and d-fructoketose have also been reported (See, Norrild and Eggert, *J. Chem. Soc. Perkin Trans* 2, page 2583 [1996]). Both the α and β fructofuranose rings have larger chemical shift values than their pyranose counterparts in the $^{13}C$ NMR spectrum (Table 4) (See, van den Berg et al., supra). In the $^{1}H$ and $^{13}C$ spectrum of the fructose complex with L-p-BPA in $D_2O$ at pH 7.4 however, only one product was detected. Since the aromatic protons of L-p-BPA are shifted upfield (from 7.73 and 7.33 ppm to 7.49 and 7.18 ppm, respectively, at pD 7.4) similar to the spectrum of L-p-BPA in alkaline solution (7.49 and 7.14 ppm at pD 11), it is contemplated that the boron atom is negatively charged and tetrahedral, although it is not necessary to understand the mechanism in order to use the present invention, and it is not intended that the present invention be so limited.

Based on the chemical shift values of the fructose complex with L-p-BPA, it appears that the carbohydrate portion of the complex adopts the β-d-fructofuranose form, although it is not necessary to understand the mechanism in order to use the present invention, and it is not intended that the present invention be so limited. This proposed β-d-fructofuranose structure of the fructose moiety of the L-p-BPA-fructose complex is in good agreement with the values for one of the complexes of p-tolylboronic acid with fructose at pD of 11–12 (complex 1, FIG. 1), as reported by Norrild and Eggert (Norrild and Eggert, supra).

Structure determination for complexes 1–3 in FIG. 1 was based on the chemical shifts in the $^{13}C$ spectrum as well as $^{1}J_{CC}$ coupling constants. The chemical shifts of complexes 1, 2 and 3 are all in accordance with a fructofuranose ring structure (Table 4). Furthermore, all three complexes display the low $^{1}J_{CC}$ values typical of vicinal diols when the O—C—C—O fragment is incorporated in a five membered ring. The only significant difference between the shifts and $^{1}J_{CC}$ coupling constants between complex 1 and complexes 2 and 3 is the low $^{1}J_{5,6}$ for complex 1. (See e.g., Norrild and Eggert, *J. Am. Chem. Soc.* 117: 1479 [1995]; Duker et al., *Carbohydr. Res.* 249: 281 [1993]; Snyder and Serianni, *Carbohydr. Res.* 163: 169 [1987]; and Krvidin and Kalabin, *Progr. NMR Spectroscopy* 21: 293 [1989]).

Although it is not necessary to understand the mechanism in order to practice the present invention, and it is not intended that the present invention be so limited, it is believed that this low $^{1}J_{CC}$ value indicates complexation that also involves C-6 in a manner such that the B—O—C-6-C-5 torsional angle approximates 60° while the O—C-6-C-5-O dihedral angle has decreased. Based on the chemical shifts of complex 1, a β-d-fructofuranose structure as shown in complex 1 (FIG. 1), was assigned to the p-tolylboronic acid and fructose complex.

TABLE 4

$^{13}C$ chemical shifts and $^{1}J_{cc}$ coupling constants (in Hz) for D-fructose and L-p-BPA-fructose in $D_2O$ at pD 7.4

| Compound | C-1 | $J_{1,2}$ | C-2 | $J_{2,3}$ | C-3 | $J_{3,4}$ | C-4 | $J_{4,5}$ | C-5 | $J_{5,6}$ | C-6 |
|---|---|---|---|---|---|---|---|---|---|---|---|
| α-D-fructofuranose[a] | 65.5 | 44.0 | 107.7 | 48.8 | 84.5 | 44.0 | 78.6 | 39.1 | 83.9 | 41.5 | 63.7 |
| β-D-fructopyranose[a] | 66.5 | 48.8 | 100.7 | 46.4 | 70.1 | 39.1 | 72.3 | 37.5 | 71.8 | 34.4 | 66.0 |
| β-D-fructofuranose[a] | 65.3 | 51.3 | 104.1 | 44.0 | 78.0 | 41.5 | 77.1 | 41.5 | 83.3 | 44.0 | 65.0 |
| 1[b] | 66.1 | 54.1 | 113.4 | 37.4 | 84.7 | 40.3 | 82.1 | 36.9 | 87.6 | 36.3 | 67.9 |
| 2[b] | 67.4 | 53.4 | 114.7 | 37.5 | 86.7 | 41.1 | 80.2 | 38.2 | 88.4 | 41.2 | 65.0 |
| 3[b] | 67.3 | 53.7 | 114.6 | 37 | 87.7 | nd | 80.4 | nd | 88.0 | 41.6 | 64.6 |
| L-p-BPA-fructose[a] | 65.7 | 53.7 | 113.5 | 36.6 | 87.6 | 36.6 | 81.5 | 39.1 | 85.0 | 36.6 | 67.2 |

[a]In $D_2O$ at pD = 7.4.
[b]In $D_2O$ at pD = 11–12.
nd = not determined.

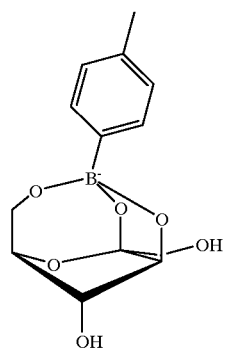

1 (82%)

TABLE 4-continued $^{13}C$ chemical shifts and $^1J_{cc}$ coupling constants (in Hz) for D-fructose and L-p-BPA-fructose in $D_2O$ at pD 7.4

| Compound | C-1 | $J_{1,2}$ | C-2 | $J_{2,3}$ | C-3 | $J_{3,4}$ | C-4 | $J_{4,5}$ | C-5 | $J_{5,6}$ | C-6 |
|---|---|---|---|---|---|---|---|---|---|---|---|

2 (13%)

3 (5%)

The strong correspondence between the NMR data obtained for the l-p-BPA-fructose complex at physiological pH and one of the complexes (e.g., as observed for p-tolylboronic acid with fructose at pD 11–12) was further investigated by a systematic study of the binding ability of fructose-containing disaccharides (Table 2). The lack of appreciable difference in binding constants for maltulose, lactulose and fructose suggests that the hydroxyl at C-4 is probably not essential to the ability of fructose to bind with l-p-BPA. However, the presence of the added 4-O-glucosyl or galactosyl group had no positive effect on binding either. The complete lack of binding for the monosaccharides methyl-α-glucopyranoside and methyl-β-galactopyranoside and disaccharide sucrose establishes that the anomeric center is essential for binding.

Although it is not necessary to understand the mechanism in order to use the present invention, and it is not contemplated that the present invention be so limited, it is believed that the presence of an anomeric center plays a critical role for complex formation, since no change in the $^1H$ NMR spectrum of l-p-BPA was observed with methyl-α-glucopyranoside, methyl-β-galactopyranoside, or sucrose. It is also contemplated that the hydroxyl at the 3-position plays a vital role in binding, as demonstrated by the decrease in binding by 1.5 $pK_{eq}$ for both turanose and leucrose. While the hydroxyl at C-3 for turanose is eliminated from binding due to the presence of the glucosyl moiety, the C-3 hydroxyl of leucrose is also unavailable for binding due to a likely significant contribution from the conformation that places the glucosyl unit in an equatorial position, resulting in a diaxial orientation between the anomeric C-2 hydroxyl and C-3 hydroxyl axial. Loss in binding ability for leucrose can also be attributed to the fructose unit being locked in the less favored pyranose ring form.

Furthermore, the similarity in binding ability between sorbose and palatinose, and a decrease of 0.5 in the $pK_{eq}$ values of these complexes, suggest that the C-6 hydroxyl is eliminated from binding by either the presence of a glucosyl unit (i.e., palatinose), or by inversion of stereochemistry at C-5 which makes binding geometrically unfeasible, although it is not necessary to understand the mechanism in order to practice the present invention, and it is not intended that the invention be so limited. Thus, this decrease of 0.5 $pK_{eq}$ in binding likely corresponds to the additional stability imparted by orthoboronate formation in the case of fructose.

Figure 2:
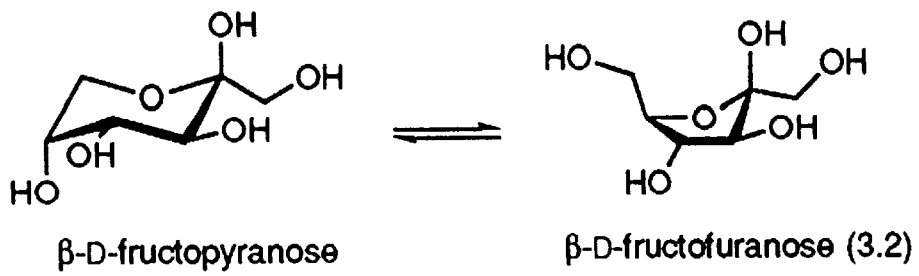
FIG. 2 shows a proposed binding conformation of carbohydrates used in the presently claimed invention (Glu=α-glucosyl; Gal=α-galactosyl).
Figure 2:
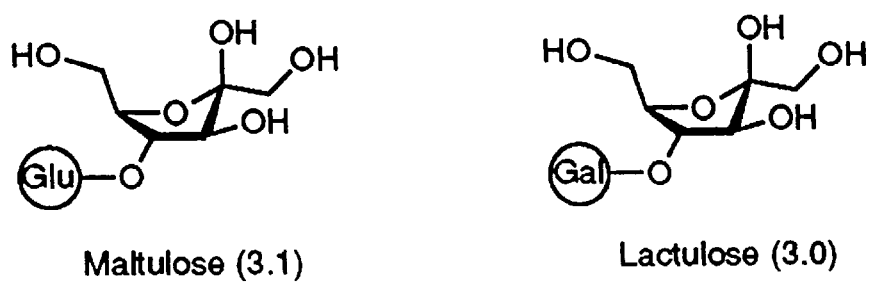
Figure 2:
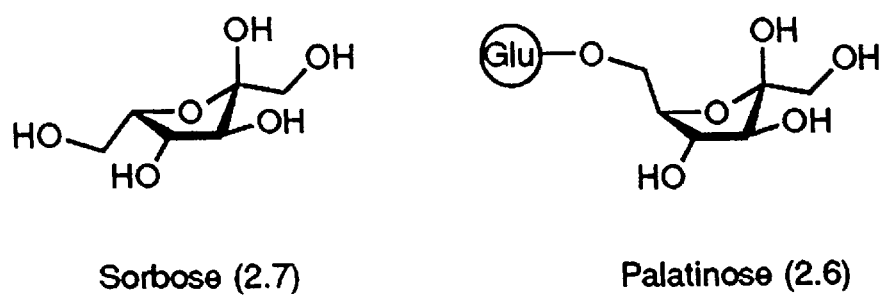
Figure 2:
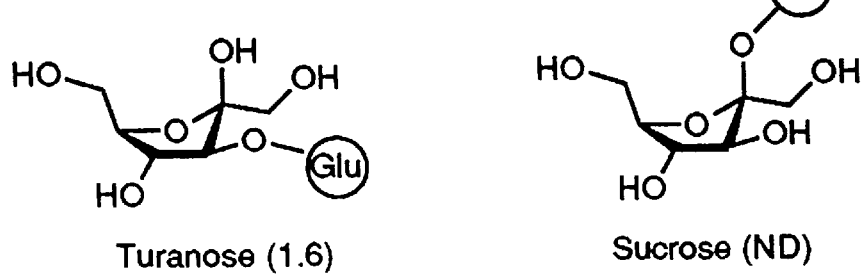
Figure 2:
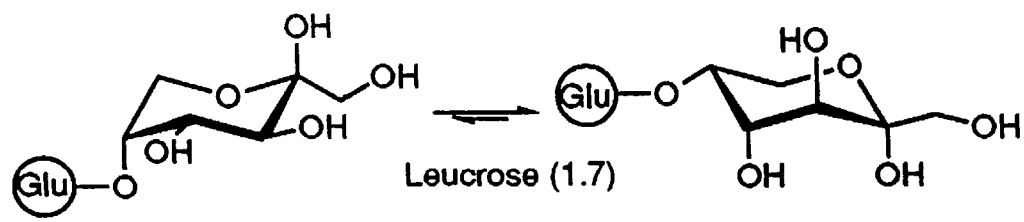
Figure 3:
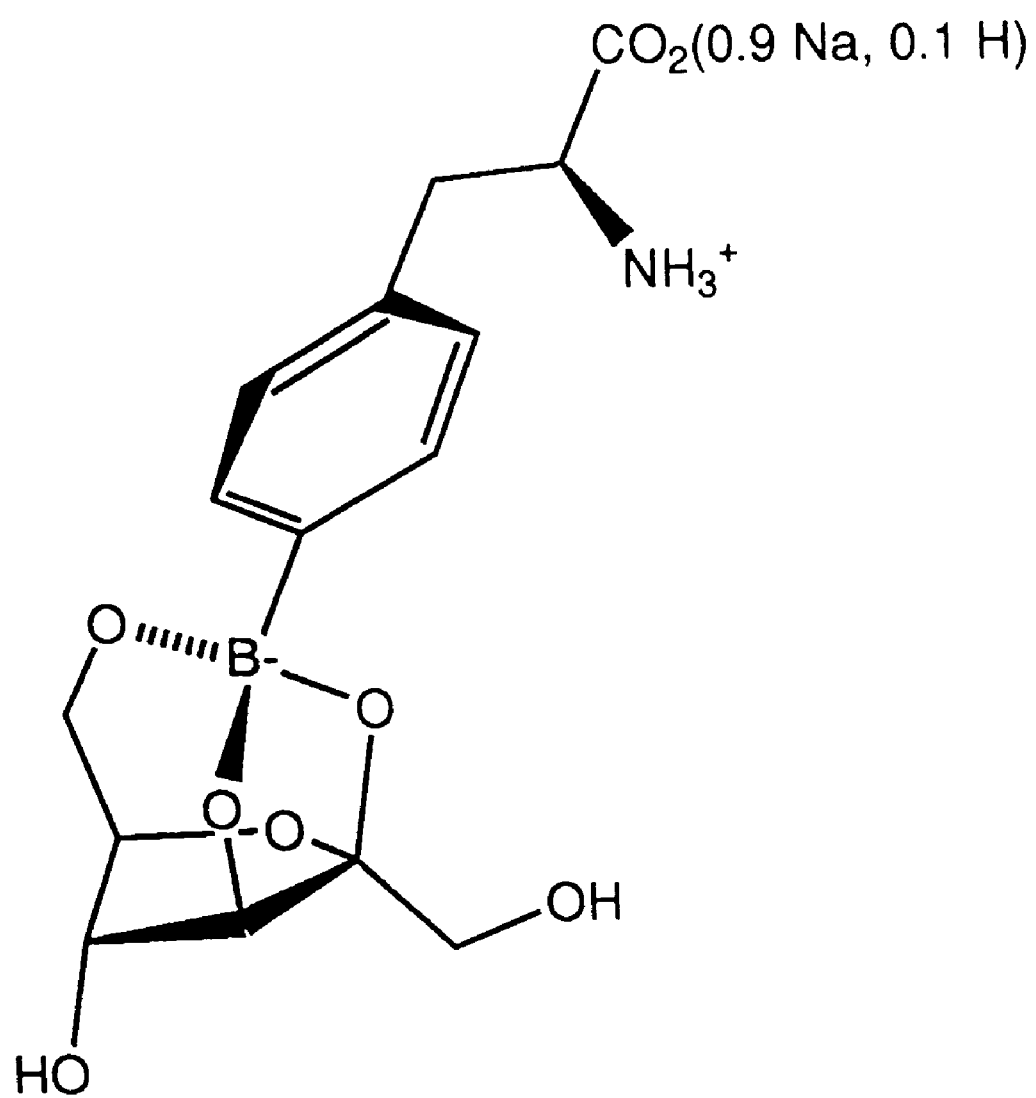
FIG. 3 shows a proposed structure of l-p-boronophenylalanine-fructose (l-p-BPA-fructose) complex in water at physiological pH.

The proposed binding conformation of some carbohydrates used in the presently claimed invention is shown in FIG. 2, and a proposed complex of l-p-BPA with fructose at physiological pH is shown in FIG. 3, although it is not necessary to understand the mechanism in order to use the present invention, and it is not contemplated that the present invention be so limited.

DEFINITIONS

The term "carbohydrates" refers to compounds of carbon, hydrogen, and oxygen that contains the saccharose unit or its first reaction product, and in which the ratio of hydrogen to oxygen is the same as in water, giving molecular formulas of $C_n(H_2O)_m$. They comprise: 1) monosaccharides, which refer to simple sugars that do not undergo hydrolysis of glycosidic bonds to give smaller sugar molecules (e.g., fructose and glucose); 2) disaccharides, sucrose, maltose, cellobiose, and lactose; and 3) polysaccharides (i.e., high polymeric substances).

As used herein, the term "polyol" refers to a polyhydric alcohol (i.e., an alcohol containing three or more hydroxyl groups). Those having three hydroxyl groups (i.e., trihydric) are glycerols; those with more than three are called sugar alcohols, with the general formula $CH_2OH(CHOH)_n CH_2OH$.

As used herein, the terms "d" and "l" (i.e., l-p-BPA) pertain to relative configurations of sugars and amino acids, based on an assumed configuration for (+)-glyceraldehytde. The "d" series has the same configuration as (+)-glyceraldehyde, and the "l" series, as (−)-glyceraldehyde. (See e.g., Wade, Jr., Organic Chemistry, pp. 383–384, Prentice-Hall, Inc. [1987]). A racemic mixture (d,l) contains both "d" and "l" configurations.

As used herein, the term "solubility" is defined as the amount of a substance (i.e., solute) that dissolves in a given volume of solvent at a given temperature. Solubility can be measured in terms of the mass (i.e., grams) of solute that dissolves per given volume or solvent, or in terms of the number of moles of solute that dissolves in a given volume of solution. The term "solubilizing" refers to the process of dissolving a substance in a given volume of solvent.

As used herein, the term "solvent" refers to a substance capable of dissolving another substance (i.e., solute) to form a uniformly dispersed mixture (i.e., solution).

As used herein, the term "solute" refers to one or more substances dissolved in another substance (i.e., solvent).

As used herein, the term "solution" refers to a uniformly dispersed mixture at the molecular or ionic level, of one or more substances (i.e., the solute) in one or more substances (i.e., the solvent).

As used herein, the terms "substantially dissolved" and "substantially solubilizing" refer to the extent that a solid substance (i.e., l-p-boronophenylalanine-carbohydrate or polyol complex) is dissolved in a liquid (e.g., water, isotonic saline or dilute saline solution), such that about less than 1% of the solid remain undissolved and suspended in solution.

As used herein, the term "freeze-drying" or "lyophilization" refers to a method of dehydration or separation of water from biological materials. The material is first frozen and then placed in a high vacuum so that the water (i.e., ice) vaporizes in the vacuum (i.e., sublimes) without melting, and the non-volatile components are left behind.

As used herein, the term "filtration" and "decanting" refer to methods for separating the components of a mixture containing a solid and a liquid. In filtration, the mixture is poured into a mesh, such as a filter paper, so that the liquid passes through and the solid is left behind. In decanting, the liquid is carefully poured out from the mixture.

As used herein, the term "acid" refers to a substance that produces hydronium ions in solution ($H_3O^+$). Acids are referred to as strong or weak according to the concentration of $H^+$ ion that results from ionization. Examples of strong acids for use in the present invention include, but are not limited to hydrochloric, sulfuric and nitric acid.

As used herein, the term "base" refers to a substance that produces hydroxide ($OH^-$) ions in an aqueous solution. Bases are referred to as strong or weak according to the concentration of hydroxyl ion that results from ionization. Examples of strong bases for use in the present invention include, but are not limited to sodium hydroxide, potassium hydroxide, magnesium hydroxide, calcium hydroxide, and ammonium hydroxide.

As used herein, the term "basic solution" refers to a solution having a pH range of about 8–14. In preferred embodiments, the basic solution for use in the presently claimed invention has a pH range of 8–10.

As used herein, the term "salt-free" refers to a solution or solid that does not contain the products of an acid-base neutralization reaction, such as NaCl, NaBr, $Na_2SO_4$, $MgSO_4$, $MgCl_2$, $CaCl_2$, etc.

As used herein, the term "essentially salt-free" and "essentially salt-free complexes" refer to complexes with 1 equivalent or less of salt (i.e., NaCl) with respect to the complex (i.e., l-p-boronophenylalanine complexes). An "essentially salt-free" l-p-boronophenylalanine-fructose complex" refers to the complex having less than 10% by weight of NaCl salt.

As used herein, the terms "complex" or "complex compound" refer to compounds formed by the bonding of a central ion with a molecule called a ligand or complexing agent. The present invention refers to l-p-boronophenylalanine complexed with carbohydrates or polyols.

As used herein, the term "pH" refers to a value representing the acidity or alkalinity of an aqueous solution, and is defined as the logarithm of the reciprocal of the hydrogen-ion concentration $[H^+]$ of a solution. The pH scale characterizes the acidity of aqueous acid-base systems, using pure water having a pH of 7, as the standard. The pH range of acids is from about 6.9 to 1, and the pH range of bases is from 7.1 to 14. Solutions that are neither acidic nor basic are "neutral," and has a pH of 7. The term "physiological pH" is used to refer to the pH of blood, which has a pH value of between 7.3 and 7.5. The term "pD" refers to a value representing the acidity or alkalinity of a deuterated solution.

As used herein, the term "equilibrium constant" or "$K_{eq}$" is a number that relates the concentrations of starting materials and products of a reversible chemical reaction to one another. For example, for a chemical reaction represented by the equation $aA+bB \rightarrow cC+dD$, the equilibrium constant would be $K=[C^c D^d]/[A^a B^b]$.

As used herein, the term "ion-exchange" refers to a reversible chemical reaction between a solid (i.e., an ion exchanger) and a liquid solution (i.e., an aqueous solution), by means of which ions may be interchanged from one substance to another. The term "ion-exchange media" refers to the means by which ion-exchange can be performed. A preferred ion-exchange media is an ion-exchange resin, although other ion-exchange media are also contemplated for use in the present invention.

As used herein, the term "ion-exchange resin" refers to resins containing active groups (e.g., sulfonic, carboxylic, phenol, or substituted amino groups), that are capable of exchanging a cation or an anion for a variety of ions brought into contact with the resin. An example of an ion-exchange resin for use in the present invention is the Dowex50WX4-50 ion exchange resin, although other ion-exchange resins performing similar function are also contemplated for use in the present invention.

As used herein, the term "isotonic" refers to the property of having the same concentration of solutes as blood (e.g., "isotonic solution" refers to a saline solution having the same concentration of solutes as blood).

As used herein, the term "iso-osmotic" refers to the property of having equal osmotic pressure. The term "iso-osmotic" solution refers to a solution having equal osmotic pressure with that of blood.

As used herein, the term "intravenous" refers to a mode of administration of a substance such as a drug or a nutrient solution, within or into a vein.

EXPERIMENTAL

The following examples are provided in order to demonstrate and further illustrate certain preferred embodiments and aspects of the present invention and are not to be construed as limiting the scope thereof.

In the experimental disclosure which follows, the following abbreviations apply: NaOH (sodium hydroxide); L-p-BPA (L-p-boronophenylalanine); B (boron); H (hydrogen); eq (equivalents); M (Molar); $\mu$M (micromolar); N (Normal); mol (moles); mmol (millimoles); $\mu$mol (micromoles); nmol (nanomoles); g (grams); mg (milligrams); $\mu$g (micrograms); ng (nanograms); l or L (liters); mL (milliliters); $\mu$L (microliters); ° C. (degrees Centigrade); h (hour or hours); m.p. (melting point); NMR (nuclear magnetic resonance); $^1$H NMR (proton nuclear magnetic resonance spectroscopy); $^{13}$C NMR (carbon-13 nuclear magnetic resonance spectroscopy); Hz (hertz); J (coupling constant); d (doublet); dd (doublet of doublets); s (singlet); br s (broad singlet); t (triplet); m (multiplet); $\delta$ (nuclear magnetic resonance chemical shift); and D$_2$O (deuterated water).

EXAMPLE 1

Preparation of $^{10}$B Enriched L-p-boronophenylalanine-D-Fructose Complex $^{10}$B enriched L-p-boronophenylalanine (0.520 g) and D-fructose (0.473 g) was suspended in distilled water (3 mL), and L-p-boronophenylalanine was dissolved by addition of 0.5 M NaOH (5.3 mL) with gentle heating. The pH of this solution is typically between 8.5 and 9.0. The pH of the solution is immediately lowered (within 2–3 minutes) to between 7.3 and 7.5 by the addition of Dowex 50WX4-50 ion exchange (H$^+$) resin with vigorous stirring. The solution is removed from the resin, and any L-p-boronophenylalanine that is suspended can be redissolved with gentle warming of the solution. The room temperature solution was then filtered through a 0.2$\mu$ filter and then freeze-dried to give sodium L-p-boronophenylalanine-D-fructose complex (0.934 g). The solid can be hydrated with warm water (60° C., solubility approximately 0.1 g/mL), and remains completely dissolved after prolonged standing (i.e., 48 hrs) at room temperature. L-p-boronophenylalanine-D-fructose complex: $^1$H NMR (buffered at pD=7.4 with NaH$_2$PO$_4$/Na$_2$HPO$_4$): $\delta$ 7.49 (d, J=7.3 Hz, 2H), 7.18 (d, J=7.3 Hz, 2H), 4.21 (br s, 1H), 4.18 (br s, 1H), 4.03–3.45 (m, 3H), 3.96 (dd, J=8.8, 5.1 Hz, 1H), 3.76 (br s, 2H), 3.28 (dd, J=14.7, 5.1 Hz, 1H), 3.012 (dd, J=14.7, 8.8 Hz, 1H); $^{13}$C NMR $\delta$ 177.0 (s), 150.7 (br s), 135.6 (s), 134.7 (d, 2C), 130.8 (d, 2C), 113.5 (s), 87.6 (d), 85.0 (d), 81.6 (d), 66.1 (t, 2C), 58.8 (d), 38.9 (t). M.p. 90–93° C.

EXAMPLE 2

Preparation of $^{10}$B Enriched L-p-boronophenylalanine-L-Sorbose Complex $^{10}$B enriched L-p-boronophenylalanine (0.520 g) and sorbose (0.473 g) was suspended in distilled water (3 mL), and L-p-boronophenylalanine was dissolved by addition of 0.5 M NaOH (5.3 mL) with gentle heating. The pH of the solution is lowered to between 7.3 and 7.5 by the addition of Dowex 50WX4-50 ion exchange (H$^+$) resin with vigorous stirring. The solution is removed from the resin, and any L-p-boronophenylalanine that is suspended can be redissolved with gentle warming of the solution. The room temperature solution was then filtered through a 0.2$\mu$ filter and then freeze-dried to give sodium L-p-boronophenylalanine-L-sorbose complex as a white solid (0.970 g). L-p-boronophenylalanine-L-sorbose complex (buffered at pD=7.4 with NaH$_2$PO$_4$/Na$_2$HPO$_4$): $^1$H NMR $\delta$ 7.55 (d, J=7.3 Hz, 2H), 7.20 (d, J=7.3 Hz, 2H), 4.29 (s, 1H), 4.09 (s, 1H), 3.95 (dd, J=8.4, 4.4 Hz, 1H), 3.3.83–3.47 (m, 5H), 3.28 (dd, J=14.7, 4.4 Hz, 1H), 3.02 (dd, J=14.7, 8.4 Hz, 1H); $^{13}$C NMR $\delta$ 177.0 (s), 150.7 (br s), 135.4 (s), 134.9 (d, 2C), 130.9 (d, 2C), 114.2 (s), 86.6 (d), 83.0 (d), 79.0 (d), 66.9 (t), 62.5 (t), 58.9 (d), 39.0 (t).

EXAMPLE 3

Preparation of $^{10}$B Enriched L-p-boronophenylalanine-D-Maltulose Complex $^{10}$B enriched L-p-boronophenylalanine (0.104 g) and D-maltulose hydrate (0.189 g) was suspended in distilled water (1 mL), and L-p-boronophenylalanine was dissolved by addition of 0.5 M NaOH (1 mL) with gentle heating. The pH of the solution is lowered to between 7.3 and 7.5 by the addition of Dowex 50WX4-50 ion exchange (H$^+$) resin with vigorous stirring. The solution is removed from the resin, and any L-p-boronophenylalanine that is suspended can be redissolved with gentle warming of the solution. The room temperature solution was then filtered through a 0.2$\mu$ filter and then freeze-dried to give sodium L-p-boronophenylalanine-D-maltulose complex as a white solid (0.245 g). L-p-boronophenylalanine-D-maltulose complex (buffered at pD=7.4 with NaH$_2$PO$_4$/Na$_2$HPO$_4$): $^1$H NMR $\delta$ 7.49 (d, J=7.6 Hz, 2H), 7.19 (d, J=7.6 Hz, 2H), 5.23 (d, J=4.4 Hz, 1H), 4.40 (br s, 1H), 4.34 (s, 1H), 4.25 (s,1H), 4.06–3.55 (m, 8H), 3.95 (dd, J=8.8, 4.7 Hz, 1H), 3.56 (dd, J=9.5, 3.7 Hz, 1H), 3.42 (dd, J=9.5, 9.5 Hz, 1H), 3.26 (dd, J=14.7, 4.7 Hz, 1H), 3.02 (dd, J=14.7, 8.8 Hz, 1H); $^{13}$C NMR $\delta$ 177.0 (s), 150.7 (br s), 135.6 (s), 134.8 (d, 2C), 130.9 (d, 2C), 113.6 (s), 99.8 (d), 86.6 (d), 86.1 (d), 75.6 (d), 75.5 (d), 74.9 (d), 74.0 (d), 72.2 (d), 66.1 (t, 2C), 63.2 (t), 58.8 (d), 38.9 (t).

EXAMPLE 4

Preparation of $^{10}$B Enriched L-p-boronophenylalanine-Lactulose Complex $^{10}$B enriched L-p-boronophenylalanine (0.208 g) and lactulose (0.360 g) was suspended in distilled water (2 mL), and L-p-boronophenylalanine was dissolved by addition of 0.5 M NaOH (2 mL) with gentle heating. The pH of the solution is lowered to between 7.3 and 7.5 by the addition of Dowex 50WX4-50 ion exchange (H$^+$) resin with vigorous stirring. The solution is removed from the resin, and any L-p-boronophenylalanine that is suspended can be redissolved with gentle warming of the solution. The room temperature solution was then filtered through a 0.2$\mu$ filter and then freeze-dried to give sodium L-p-boronophenylalanine-lactulose complex as a white solid (0.499 g). L-p-boronophenylalanine-lactulose complex (buffered at pD=7.4 with NaH$_2$PO$_4$/Na$_2$HPO$_4$): $^1$H NMR $\delta$ 7.48 (d, J=7.3 Hz, 2H), 7.19 (d, J=7.3 Hz, 2H), 4.52 (dd, J=6.6, 1.5 Hz, 1H), 4.47 (s, 1H), 4.37 (br s, 1H), 4.33 (s, 1H), 4.02–3.92 (m, 3H), 3.86–3.50 (m, 6H), 3.52 (dddd, J=9.5, 8.0, 8.0, 1.7 Hz, 1H), 3.27 (dd, J=14.7, 2.9 Hz, 1H), 3.02 (dd, J=14.7, 8.8 Hz, 1H); $^{13}$C NMR $\delta$ 177.0 (s), 150.7 (br s), 135.7 (s), 134.8 (d, 2C), 130.9 (d, 2C), 113.5 (s), 105.5 (d), 89.7 (d), 86.0 (d), 78.0 (d), 75.3 (d, 2C), 73.4 (d), 71.3 (d), 66.0 (t, 2C), 63.8 (t), 58.8 (d), 39.0 (t).

EXAMPLE 5

Preparation of $^{10}$B Enriched L-p-boronophenylalanine-D-Palatinose Complex $^{10}$B enriched L-p-boronophenylalanine (0.104 g) and D-palatinose hydrate (0.189 g) was suspended in distilled water (1 mL), and l-p-boronophenylalanine was dissolved by addition of 0.5 M NaOH (1 mL) with gentle heating. The pH of the solution is lowered to between 7.3 and 7.5 by the addition of Dowex 50WX4-50 ion exchange (H⁺) resin with vigorous stirring. The solution is removed from the resin, and any l-p-boronophenylalanine that is suspended can be redissolved with gentle warming of the solution. The room temperature solution was then filtered through a 0.2μ filter and then freeze-dried to give sodium l-p-boronophenylalanine-d-palatinose complex as a white solid (0.233 g). l-p-boronophenylalanine-palatinose complex (buffered at pD=7.4 with $NaH_2PO_4/Na_2HPO_4$): $^1H$ NMR δ 7.52 (d, J=7.3 Hz, 2H), 7.19 (d, J=7.3 Hz, 2H), 4.34 (s, 1H), 4.21–4.05 (m, 3H), 3.96 (dd, J=8.8, 4.3 Hz, 1H), 3.96–3.46 (m, 9H), 3.40 (dd, J=14.7, 9.5 Hz, 1H), 3.28 (dd, J=14.7, 4.3 Hz, 1H), 3.02 (dd, J=14.7, 8.8 Hz, 1H), $^{13}C$ NMR δ 177.0 (s), 150.7 (br s), 135.2 (s), 134.9 (d, 2C), 130.8 (d, 2C), 114.5 (s), 100.9 (d), 86.7 (d), 85.8 (d), 80.3 (d), 75.6 (d), 74.3 (d), 74.1 (d), 72.1 (d), 70.5 (t), 67.1 (t), 62.9 (t), 58.8 (d), 38.9 (t).

EXAMPLE 6

Preparation of $^{10}B$ Enriched l-p-boronophenylalanine-d-Sorbitol Complex $^{10}B$ enriched l-p-boronophenylalanine (0.104 g) and sorbitol (0.096 g) was suspended in distilled water (1 mL), and l-p-boronophenylalanine was dissolved by addition of 0.5 M NaOH (1 mL) with gentle heating. The pH of the solution is lowered to between 7.3 and 7.5 by the addition of Dowex 50WX4-50 ion exchange (H⁺) resin with vigorous stirring. The solution is removed from the resin, and any l-p-boronophenylalanine that is suspended can be redissolved with gentle warming of the solution. The room temperature solution was then filtered through a 0.21μ filter and then freeze-dried to give sodium l-p-boronophenylalanine-d-sorbitol complex as a white solid (0.182 g). l-p-boronophenylalanine-d-sorbitol complex (buffered at pD=7.4 with $NaH_2PO_4/Na_2HPO_4$): $^1H$ NMR δ 7.51 (d, J=7.3 Hz, 2H), 7.19 (d, J=7.3 Hz, 2H), 4.09 (br s, 1H), 3.95–3.42 (m, 7H), 3.93 (dd, J=8.1, 5.1 Hz, 1H), 3.25 (dd, J=14.6, 5.1 Hz, 1H), 3.02 (dd, J=14.6, 8.1 Hz, 1H). $^{13}C$ NMR δ:

EXAMPLE 7

Preparation of $^{10}B$ Enriched l-p-boronophenylalanine-d-Mannitol Complex $^{10}B$ enriched l-p-boronophenylalanine (0.104 g) and mannitol (0.096 g) was suspended in distilled water (1 mL), and l-p-boronophenylalanine was dissolved by addition of 0.5 M NaOH (1 mL) with gentle heating. The pH of the solution is lowered to between 7.3 and 7.5 by the addition of Dowex 50WX4-50 ion exchange (H⁺) resin with vigorous stirring. The solution is removed from the resin, and any l-p-boronophenylalanine that is suspended can be redissolved with gentle warming of the solution. The room temperature solution was then filtered through a 0.2μ filter and then freeze-dried to give sodium l-p-boronophenylalanine-d-mannitol complex as a white solid (0.186 g). l-p-boronophenylalanine-d-mannitol complex (buffered at pD=7.4 with $NaH_2PO_4/Na_2HPO_4$): $^1H$ NMR δ 7.51 (d, J=6.6 Hz, 2H), 7.21 (d, J=6.6 Hz, 2H), 4.05–3.60 (m, 8H), 3.96 (dd, J=8.4, 4.4 Hz, 1H), 3.26 (dd, J=13.9, 4.4 Hz, 1H), 3.04 (dd, J=13.8, 8.4 Hz, 1H); $^{13}C$ NMR δ 177.0 (s), 150.7 (br s), 135.9 (s), 135.1 (d, 2C), 131.0 (d, 2C), 78.3 (d), 74.3 (d), 73.5 (d), 71.9 (d), 66.4 (t), 65.9 (t), 58.8 (d), 39.0 (t).

EXAMPLE 8

Preparation of $^{10}B$ Enriched l-p-boronophenylalanine-Dulcitol Complex $^{10}B$ enriched l-p-boronophenylalanine (0.104 g) and dulcitol (0.096 g) was suspended in water (1 mL), and l-p-boronophenylalanine dissolved by addition of 0.5 M NaOH (1 mL) with gentle heating. The pH of the solution is lowered to between 7.3 and 7.5 by the addition of Dowex 50WX4-50 ion exchange (H⁺) resin with vigorous stirring. The solution is removed from the resin, and any l-p-boronophenylalanine that is suspended can be redissolved with gentle warming of the solution. The room temperature solution was then filtered through a 0.2μ filter and then freeze-dried to give sodium l-p-boronophenylalanine-dulcitol complex as a white solid (0.198 g). l-p-boronophenylalanine-dulcitol complex (buffered at pD=7.4 with $NaH_2PO_4/Na_2HPO_4$): $^1H$ NMR δ 7.50 (d, J=6.9 Hz, 2H), 7.19 (d, J=6.9 Hz, 2H), 4.02–3.87 (m, 2H), 3.95 (dd, J=8.4, 4.4 Hz, 1H), 3.66 (br s, 6H), 3.27 (dd, J=14.7, 4.4 Hz, 1H), 3.02 (dd, J=14.7, 8.4 Hz, 1H); $^{13}C$ NMR δ 177.0 (s), 150.7 (br s), 135.8 (s), 135.1 (d, 2C), 130.9 (d, 2C), 72.8 (d), 72.1 (d), 65.9 (t), 58.8 (d), 39.0 (t).

EXAMPLE 9

Preparation of $^{10}B$ Enriched l-p-boronophenylalanine-Xylitol Complex $^{10}B$ enriched l-p-boronophenylalanine (0.104 g) and xylitol (0.080 g) was suspended in distilled water (1 mL), and l-p-boronophenylalanine dissolved by addition of 0.5 M NaOH (1 mL) with gentle heating. The pH of the solution is lowered to between 7.3 and 7.5 by the addition of Dowex 50WX4-50 ion exchange (H⁺) resin with vigorous stirring. The solution is removed from the resin, and any l-p-boronophenylalanine that is suspended can be redissolved with gentle warming of the solution. The room temperature solution was then filtered through a 0.2μ filter and then freeze-dried to give sodium l-p-boronophenylalanine-xylitol complex as a white solid (0.168 g). l-p-boronophenylalanine-xylitol complex (buffered at pD=7.4 with $NaH_2PO_4/Na_2HPO_4$): $^1H$ NMR δ 7.50 (d, J=6.9 Hz, 2H), 7.19 (d, J=6.9 Hz, 2H), 3.96 (m, 3H), 3.87–3.64 (m, 4H), 3.27 (dd, J=14.7, 4.4 Hz, 1H), 3.02 (dd, J=14.7, 8.4 Hz, 1H); $^{13}C$ NMR δ 177.0 (s), 150.7 (br s), 135.8 (s), 135.1 (d, 2C), 130.9 (d, 2C), 77.8 (d), 74.6 (d), 73.4 (d), 65.8 (t), 65.3 (t), 58.8 (d), 39.0 (t).

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the art of synthetic chemistry and/or related fields are intended to be within the scope of the following claims.

What is claimed is:

1. A method of making essentially salt-free carbohydrate and polyol (p-boronophenylalanine) complexes, comprising:

a) providing:
  i) p-boronephenylalanine,
  ii) water,
  iii) a compound selected from the group consisting of carbohydrates and polyols,
  iv) a base, and
  v) an ion-exchange media;
b) mixing said p-boronophenylalanine, said water, said compound, and said base, to produce a basic solution, such that said p-boronophenylalanine and said compound are substantially dissolved in said basic solution;
c) adding said ion-exchange media to said basic solution, thereby adjusting the pH of said basic solution to the range of between about 7.3 and 7.5, to produce a mixture at physiological pH; and
d) removing said ion-exchange media from said mixture to produce an essentially salt-free (p-boronophenylalanine) complex in solution.

2. The method of claim 1, further comprising the step of:
e) freeze-drying said essentially salt-free (p-boronophenylalanine) complex in solution, to produce a freeze-dried essentially salt-free (p-boronophenylalanine) complex.

3. The method according to claim 1, wherein said removing step comprises filtration.

4. The method of claim 1, wherein said removing step comprises decanting.

5. The method according to claim 1, wherein said ion-exchange media comprises an ion-exchange resin.

6. The method according to claim 5, wherein said ion-exchange resin is Dowex 50WX4-50 ion-exchange resin.

7. The method according to claim 1, wherein said basic solution comprises 1 equivalent of said p-boronophenylalanine and approximately 1.1 equivalents of said compound.

8. The method according to claim 1, wherein said basic solution comprises 1 equivalent of said p-boronophenylalanine and an excess of up to 8 equivalents of said compound.

9. The method according to claim 1, wherein said basic solution has a pH of between about 8 and 10.

10. The method according to claim 1, wherein said compound is selected from the group consisting of monosaccharides, disaccharides, fructose, sorbose, ribose, galactose, glucose, mannose, 2-deoxygalactose, 2-deoxyglucose, maltulose, lactulose, palatinose, leucrose, turanose, lactose, maltose, sorbitol, mannitol, dulcitol, xylitol, adonitol and threitol.

11. The method according to claim 1, wherein said base is selected from the group consisting of NaOH, KOH, Ca(OH)$_2$ and Mg(OH)$_2$.

12. The method according to claim 1, wherein said p-boronophenylalanine is selected from the group consisting of (d,l)-p-boronophenylalanine and l-p-boronophenylalanine.

13. A composition comprising an essentially salt-free carbohydrate-(p-boronophenylalanine) complex synthesized using the method of claim 1.

14. A freeze-dried essentially salt-free p-boronophenylalanine complex selected from the group consisting of l-p-boronophenylalanine-d-fructose complex, l-p-boronophenylalanine-d-sorbose complex, l-p-boronophenylalanine-d-maltulose complex, l-p-boronophenylalanine-d-lactulose complex, l-p-boronophenylalanine-d-palatinose complex, l-p-boronophenylalanine-d-sorbitol complex, l-p-boronophenylalanine-d-mannitol complex, l-p-boronophenylalanine-dulcitol complex, and l-p-boronophenylalanine-xylitol complex.

15. A method of solubilizing an essentially salt-free (l-p-boronophenylalanine)-carbohydrate complex, comprising the steps of:
a) providing, in any order:
  i) a freeze-dried essentially salt-free (l-p-boronophenylalanine)-carbohydrate complex, and
  ii) a solvent, said solvent is selected from the group consisting of water, isotonic saline, and dilute saline;
b) substantially solubilizing said freeze-dried salt-free (l-p-boronophenylalanine)-carbohydrate complex with said solvent, to provide an iso-osmotic solution.

16. The method of claim 15, wherein said freeze-dried salt-free (l-p-boronophenylalanine)-carbohydrate complex is complexed to a carbohydrate selected from the group consisting of monosaccharides, disaccharides, fructose, sorbose, ribose, galactose, glucose, mannose, 2-deoxygalactose, 2-deoxyglucose, maltulose, lactulose, palatinose, leucrose, turanose, lactose and maltose.

17. The method of claim 15, wherein said iso-osmotic solution is suitable for intravenous use.

18. A method comprising the steps of:
a) providing, in any order:
  i) a freeze-dried essentially salt-free (l-p-boronophenylalanine)-polyol complex, and
  ii) a solvent, said solvent is selected from the group consisting of water, isotonic saline, and dilute saline;
b) substantially solubilizing said freeze-dried salt-free (l-p-boronophenylalanine)-polyol complex with said solvent, to provide an iso-osmotic solution.

19. The method of claim 18, wherein said iso-osmotic solution is suitable for intravenous use.

20. The method of claim 18, wherein said essentially freeze-dried salt-free (l-p-boronophenylalanine)-polyol complex is complexed to a polyol selected from the group consisting of sorbitol, mannitol, dulcitol, xylitol, adonitol and threitol.

21. A composition comprising an essentially salt-free polyol-p-boronophenylalanine) complex synthesized using the method of claim 1.

* * * * *